US007238656B2

(12) United States Patent
Wormser

(10) Patent No.: US 7,238,656 B2
(45) Date of Patent: Jul. 3, 2007

(54) PROTECTIVE FACTORS AGAINST INFLAMMATION, BURNS AND NOXIOUS STIMULI

(75) Inventor: Uri Wormser, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 329 days.

(21) Appl. No.: 10/790,888

(22) Filed: Mar. 1, 2004

(65) Prior Publication Data

US 2005/0118277 A1 Jun. 2, 2005

Related U.S. Application Data

(63) Continuation of application No. PCT/IL02/00713, filed on Aug. 29, 2002.

(30) Foreign Application Priority Data

Aug. 29, 2001 (IL) ..................................... 145181

(51) Int. Cl.
*A61K 38/04* (2006.01)

(52) U.S. Cl. ......................................................... 514/2

(58) Field of Classification Search ..................... None
See application file for complete search history.

(56) References Cited

U.S. PATENT DOCUMENTS

| | | | | |
|---|---|---|---|---|
| 6,468,537 B1 * | 10/2002 | Datta et al. | .............. | 424/185.1 |
| 2003/0007964 A1 | 1/2003 | Bae et al. | ................ | 424/94.61 |
| 2004/0039157 A1 * | 2/2004 | Staton et al. | ............... | 530/324 |

FOREIGN PATENT DOCUMENTS

WO WO 01/38522 5/2001

OTHER PUBLICATIONS

Citron "Alzheimer's disease: treatments in discovery and development." Nature Neurosci. 2002, 5, 1055.*

Rizzello, et al. "The management of refractory Crohn's disease." Ailment Pharmacol. Ther. 2002, 16, 40.*

Korczyn & Nussbaum "Emerging therapies in the pharmacological treatment of Parkinson's Disease." Drugs, 2002, 62(5), 775.*

Skuk et al. "Experimental and therapeutic approaches to muscular dystrophies." Curr. Op. Neur. 2002 15, 563.*

Coussens & Werb "Inflammation and cancer." Nature 2002, 420, 860.*

Wiendl & Hohlfeld "Therapeutic approaches in multiple sclerosis." Biodrugs 2002, 16(3) 183.*

Ashcroft et al. "Therapeutic strategies for psoriasis." J. Clin. Pharm. Ther. 2000, 25, 1.*

Masuda & Sugiyama "Human fibrinopeptide A mediates allergic reaction in mice in the acute phase." Peptides 2001, 22, 1511.*

Scherer et al. "The effect of fibrinopeptides A and B on experimental allergic encephalomyelitis" Clin. exp. Immunol. 1980, 40, 49.*

Steinman et al. "How to successfully apply animal studies in experimental allergic encephalomyelitis to research on multiple sclerosis." Ann. Neurol. 2006, 60(1), 12-21.*

Myers et al. Collagen-induced arthritis, an animal model of autoimmunity. Life Sci. 1997, 61(19), 1861-78.*

Elgjo, K., et al., "Proliferation-dependent efect of skin extracts (chalone) on mouse epidermal cell flux at the G1-S, S-G2 and G2-M transitions", Virchows Archiv. B. 1983, vol. 42, No. 2, pp. 143-151, abstract only.

* cited by examiner

*Primary Examiner*—Cecilia J. Tsang
*Assistant Examiner*—Christina Marchetti Bradley
(74) *Attorney, Agent, or Firm*—Winston & Strawn LLP

(57) ABSTRACT

Peptide factors isolated from skin following exposure to chemical or thermal injury and treatment with iodine preparations are capable of reducing or ameliorating the extent of injury when administered to other animals. Specific peptides, including fragments of histone H2A and fibrinopeptide A, and preferred derivatives of these peptides are disclosed. The extracts, peptides and pharmaceutical compositions according to the invention are useful for the preparation and treatment of inflammatory conditions and exposure to noxious stimuli.

13 Claims, 8 Drawing Sheets

```
                         SEQUENCE LISTING

<160> NUMBER OF SEQ ID NOS: 14

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Lys Gly Asn Tyr Ala Glu Arg Ile Ala
1               5


<210> SEQ ID NO 2
<211> LENGTH: 12
<212> TYPE: PRT
<213> ORGANISM: Artificial Sequence
<220> FEATURE:
<223> OTHER INFORMATION: Synthetic peptide

<400> SEQUENCE: 2

Asp Thr Glu Phe Glu Ala Ala Gly Gly Gly Val Arg
1               5                   10


<210> SEQ ID NO 3
<211> LENGTH: 13
<212> TYPE: PRT
<213> ORGANISM: Artificial Sequence
<220> FEATURE:
<223> OTHER INFORMATION: Synthetic peptide

<400> SEQUENCE: 3

Thr Asp Thr Glu Phe Glu Ala Ala Gly Gly Gly Val Arg
1               5                   10


<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Thr Thr Asp Thr Glu Phe Glu Ala Ala Gly Gly Gly Val Arg
1               5                   10


<210> SEQ ID NO 5
<211> LENGTH: 9
<212> TYPE: PRT
<213> ORGANISM: Artificial Sequence
<220> FEATURE:
<221> NAME/KEY: MOD_RES
<222> LOCATION: (5)..(5)
<223> OTHER INFORMATION: METHYLATION, MeAla
```

-continued

<220> FEATURE:
<223> OTHER INFORMATION: Synthetic peptide

<400> SEQUENCE: 5

Lys Gly Asn Tyr Ala Glu Arg Ile Ala
1 5

<210> SEQ ID NO 6
<211> LENGTH: 9
<212> TYPE: PRT
<213> ORGANISM: Artificial Sequence
<220> FEATURE:
<221> NAME/KEY: MOD_RES
<222> LOCATION: (8)..(8)
<223> OTHER INFORMATION: METHYLATION, MeIle
<220> FEATURE:
<223> OTHER INFORMATION: Synthetic peptide

<400> SEQUENCE: 6

Lys Gly Asn Tyr Ala Glu Arg Ile Ala
1 5

<210> SEQ ID NO 7
<211> LENGTH: 9
<212> TYPE: PRT
<213> ORGANISM: Artificial Sequence
<220> FEATURE:
<221> NAME/KEY: MOD_RES
<222> LOCATION: (2)..(2)
<223> OTHER INFORMATION: METHYLATION, MeGly
<220> FEATURE:
<223> OTHER INFORMATION: Synthetic peptide

<400> SEQUENCE: 7

Lys Gly Asn Tyr Ala Glu Arg Ile Ala
1 5

<210> SEQ ID NO 8
<211> LENGTH: 9
<212> TYPE: PRT
<213> ORGANISM: Artificial Sequence
<220> FEATURE:
<221> NAME/KEY: MOD_RES
<222> LOCATION: (2)..(2)
<223> OTHER INFORMATION: METHYLATION, MeGly
<220> FEATURE:
<221> NAME/KEY: MOD_RES
<222> LOCATION: (8)..(8)
<223> OTHER INFORMATION: METHYLATION, MeIle
<220> FEATURE:
<223> OTHER INFORMATION: Synthetic peptide

<400> SEQUENCE: 8

Lys Gly Asn Tyr Ala Glu Arg Ile Ala
1 5

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Ala Asp Ser Gly Glu Gly Asp Phe Leu Ala Glu Gly Gly Gly Val
1 5 10 15

<210> SEQ ID NO 10
<211> LENGTH: 9

-continued

```
<212> TYPE: PRT
<213> ORGANISM: Artificial Sequence
<220> FEATURE:
<223> OTHER INFORMATION: Synthetic peptide

<400> SEQUENCE: 10

Lys Gly Asn Tyr Ala Glu Arg Val Gly
1               5


<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Lys Gly Asn Tyr Ser Glu Arg Val Gly
1               5


<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Lys Ala His Tyr Ser Glu Arg Val Gly
1               5


<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Lys Gly His Tyr Ala Glu Arg Val Gly
1               5


<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Lys Ser Arg Thr Thr Ser His Gly Arg Val Gly
1               5                   10
```

PROTECTIVE FACTORS AGAINST INFLAMMATION, BURNS AND NOXIOUS STIMULI

CROSS-REFERENCE TO RELATED APPLICATIONS

This application is a continuation of International application PCT/IL02/00713 filed Aug. 29, 2002, the entire content of which is expressly incorporated herein by reference thereto.

FIELD OF THE INVENTION

The present invention relates to pharmaceutical compositions comprising peptides and their derivatives, and to the use of these compositions for treatment of tissue lesions or diseases caused by, or associated with inflammatory processes including, but not limited to, those resulting from chemical burns, thermal burns and additional noxious stimuli.

BACKGROUND OF THE INVENTION

Chemical and thermal burns are common accidents that cause huge suffering and expense (medical treatments, loss of working days, etc.). The inventor has previously demonstrated that topical application of either iodine or povidone iodine preparations immediately after exposure to heat significantly reduces the burning sensation, and more importantly, the skin damage that was expected to develop without the iodine treatment [Wormser, U. (1998) Burns 24, 383]. The antidotal effect of iodine preparations was also demonstrated for lesions induced by mustard gas (sulfur mustard), and non-mustard vesicants. In addition, post-exposure treatment with topical iodine preparations was found to significantly reduce the degree of skin lesions caused by the chemical agents [Wormser U et al. (1997) Arch. Toxicol. 71, 165–170; Wormser U et al. (2000) Toxicol. Appl. Pharmacol. 169, 33–39].

These findings could lead to the hypothesis that topical treatment of thermal or chemical skin burns with iodine preparations produces factors, which protect the tissue against such burns.

While a variety of peptides useful in the treatment of malignancies and bacteriological infections have been disclosed, nowhere in the background art is it taught or suggested that peptides produced and/or released by skin in response to thermal injury after treatment with iodine preparations may be useful for the prevention of tissue trauma or damage induced by chemical or thermal insults.

The inventor now shows that these novel anti-inflammatory peptides are useful alone or in conjunction with known anti-inflammatory agents for the prevention and treatment of tissue damage as a result of inflammatory processes and noxious stimuli.

SUMMARY OF THE INVENTION

It is an object of the present invention to provide factors that protect against inflammatory processes including those caused by thermal or chemical burns. It is a further object of the present invention to provide factors that protect against inflammatory damage caused by additional noxious stimuli. It is yet a further object of the present invention to provide factors, which are isolated from the skin after exposure to thermal injury, capable of reducing or ameliorating damage due to inflammatory processes including those due to thermal or chemical burns. It is another object of the present invention to provide factors, which are isolated from the skin after exposure to thermal or chemical injury and treatment with iodine preparations, capable of reducing or ameliorating damage due to inflammation and inflammatory processes including but not limited to that caused by thermal or chemical burns. It is yet another object of the present invention to identify these factors, to characterize them and to prepare pharmaceutical compositions comprising the factors and/or their homologs and derivatives.

According to the principles of the present invention it is now disclosed that peptide factors isolated from skin following exposure to chemical or thermal injury and treatment with iodine preparations are capable of reducing or ameliorating the extent of injury if administered to the skin of other animals. It is emphasized that while the principles of the invention are exemplified herein below through the use of animal models the invention is useful for humans, and that the human homologs of all disclosed peptides are explicitly included within the scope of the invention.

According to certain currently preferred embodiments of the present invention the peptides isolated from the skin are selected from the group consisting of:

| | |
|---|---|
| H-Lys-Gly-Asn-Tyr-Ala-Glu-Arg-Ileu-Ala-OH (peptide III) | SEQ ID NO:1 |
| H-Asp-Thr-Glu-Phe-Glu-Ala-Ala-Gly-Gly-Gly-Val-Arg-OH (peptide IV) | SEQ ID NO:2 |
| H-Thr-Asp-Thr-Glu-Phe-Glu-Ala-Ala-Gly-Gly-Gly-Val-Arg-OH (peptide VI) | SEQ ID NO:3 |
| H-Thr-Thr-Asp-Thr-Glu-Phe-Glu-Ala-Ala-Gly-Gly-Gly-Val-Arg-OH (peptide VII) | SEQ ID NO:4 |

Peptide III was found to be a partial sequence of Histone H2A with its carboxy terminal Gly was substituted by Ala. Peptide VI was identified as guinea pig fibrinopeptide A, while peptides IV and VII differ from peptide VI by omission and addition, respectively, of an amino terminal threonine. It will be understood that within the scope of the present invention the peptides may be elongated or truncated by one or more residues without altering their basic protective attributes. Active fragments, as well as deletions or substitutions as well as derivatives are also possible without detracting from the activity of the specific disclosed peptides.

According to additional currently more preferred embodiments of the invention the peptides are selected from the group consisting of:

SEQ ID NO:5

3b H-$Lys^1$-$Gly^2$-$Asn^3$-$Tyr^4$-*Me*$Ala^5$-$Glu^6$-$Arg^7$-$Ileu^8$-$Ala^9$-OH

SEQ ID NO:6

3g H-$Lys^1$-$Gly^2$-$Asn^3$-$Tyr^4$-$Ala^5$-$Glu^6$-$Arg^7$-*Me*$Ileu^8$-$Ala^9$-OH

SEQ ID NO:7

3d H-$Lys^1$-*Me*$Gly^2$-$Asn^3$-$Tyr^4$-$Ala^5$-$Glu^6$-$Arg^7$-$Ileu^8$-$Ala^9$-OH -continued

SEQ ID NO:8

3e H-Lys$^1$-*Me*Gly$^2$-Asn$^3$-Tyr$^4$-Ala$^5$-Glu$^6$-Arg$^7$-*Me*Ileu$^8$-Ala$^9$-OH wherein Me denotes an N-methylated amino acid residue.

Particularly preferred are human homologues of these protective peptides:

| | |
|---|---|
| H-Ala-Asp-Ser-Gly-Glu-Gly-Asp-Phe-Leu-Ala-Glu-Gly-Gly-Gly-Val-OH (Human Fibrinopeptide A) | SEQ ID NO:9 |
| H-Lys-Gly-Asn-Tyr-Ala-Glu-Arg-Val-Gly-OH (Human H2A) | SEQ ID NO:10 |
| H-Lys-Gly-Asn-Tyr-Ser-Glu-Arg-Val-Gly-OH (peptide 3m) (Human H2A) | SEQ ID NO:11 |
| H-Lys-Ala-His-Tyr-Ser-Glu-Arg-Val-Gly-OH (Human H2A) | SEQ ID NO:12 |
| H-Lys-Gly-His-Tyr-Ala-Glu-Arg-Val-Gly-OH (peptide 3ml) (Human H2A) | SEQ ID NO:13 |
| H-Lys-Ser-Arg-Thr-Thr-Ser-His-Gly-Arg-Val-Gly-OH (Human H2A) | SEQ ID NO:14 |

It is explicitly understood that any known peptides, such as Fibrinopeptide A designated herein by SEQ ID NO:3 or SEQ ID NO:9, are excluded from the novel compounds, but are disclosed and claimed for all of the novel uses disclosed herein.

Methods of using these peptides are also disclosed, comprising administering to an individual in need thereof a therapeutically effective amount of a pharmaceutical composition comprising as an active ingredient a peptide according to the invention. Preferably the individual is a human subject and the peptide is a human homolog or analog of the sequences disclosed herein. Alternatively and preferably, the pharmaceutical compositions may further comprise at least one additional agent or drug, including but not limited to known anti-inflammatory agents, or chemokine/cytokine modulatory agents.

The compounds are useful as drugs for preventing, treating or managing the symptoms in patients having chronic inflammatory and/or autoimmune diseases or disorders. By virtue of their anti-inflammatory properties it will be recognized that the compositions according to the present invention will be useful for treating a diverse group of indications having an inflammatory or autoimmune mechanism involved in their etiology or pathogenesis exemplified by psoriasis, systemic lupus erthematosus (SLE), multiple sclerosis, inflammatory bowel disease (Crohn's disease) and arthritis, including rheumatoid arthritis, asthma, and certain degenerative diseases including amyotrophic lateral sclerosis, Parkinson's disease, Alzheimer's disease and muscular dystrophy, as well as sepsis and malignant or benign tumors having inflammatory component or involving inflammatory processes.

The compositions of the invention are particularly useful for preventing, reducing or treating the tissue damage consequent to trauma or other noxious insults including but not limited to heat stimuli, cold stimuli, chemical stimuli, electric stimuli, ultraviolet irradiation, ionizing and non-ionizing irradiation, and ultrasound.

DETAILED DESCRIPTION OF THE INVENTION

The present invention relates to peptides and their derivatives capable of protecting tissue against noxious stimuli. More particularly, the present invention provides peptides and their derivatives that, by administration to the body, reduce the degree, or prevents the development of lesions caused by many kinds of noxious stimuli including heat, one or more chemicals, irradiation and combinations of these stimuli.

The inventor has previously demonstrated that topical application of iodine or povidone iodine preparations immediately after exposure to heat reduces, and many times nullifies, the burning sensation and more importantly, prevents or significantly reduces, skin damage that was expected to develop without iodine treatment [Wormser, U. (1998) Burns 24, 383]. The antidotal effect of iodine preparations was also demonstrated against mustard gas (sulfur mustard) and non-mustard vesicants. It was shown that post-exposure treatment with topical iodine preparations significantly reduced the degree of skin lesion caused by the chemical agents [Wormser U et al. (1997) Arch. Toxicol. 71, 165–170; Wormser U et al. (2000) Toxicol. Appl. Pharmacol. 169, 33–39].

These findings led to the assumption that protective factors are produced in the skin upon heat or chemical stimuli followed by topical treatment with iodine preparation.

To verify this hypothesis guinea pig skin was exposed to heat and immediately thereafter applied with iodine. Extracts of the skin were injected intradermally into new, naive guinea pigs. Immediately thereafter the guinea pigs were exposed to heat stimuli; the animals were checked for gross pathology during the following days.

Figure 1:
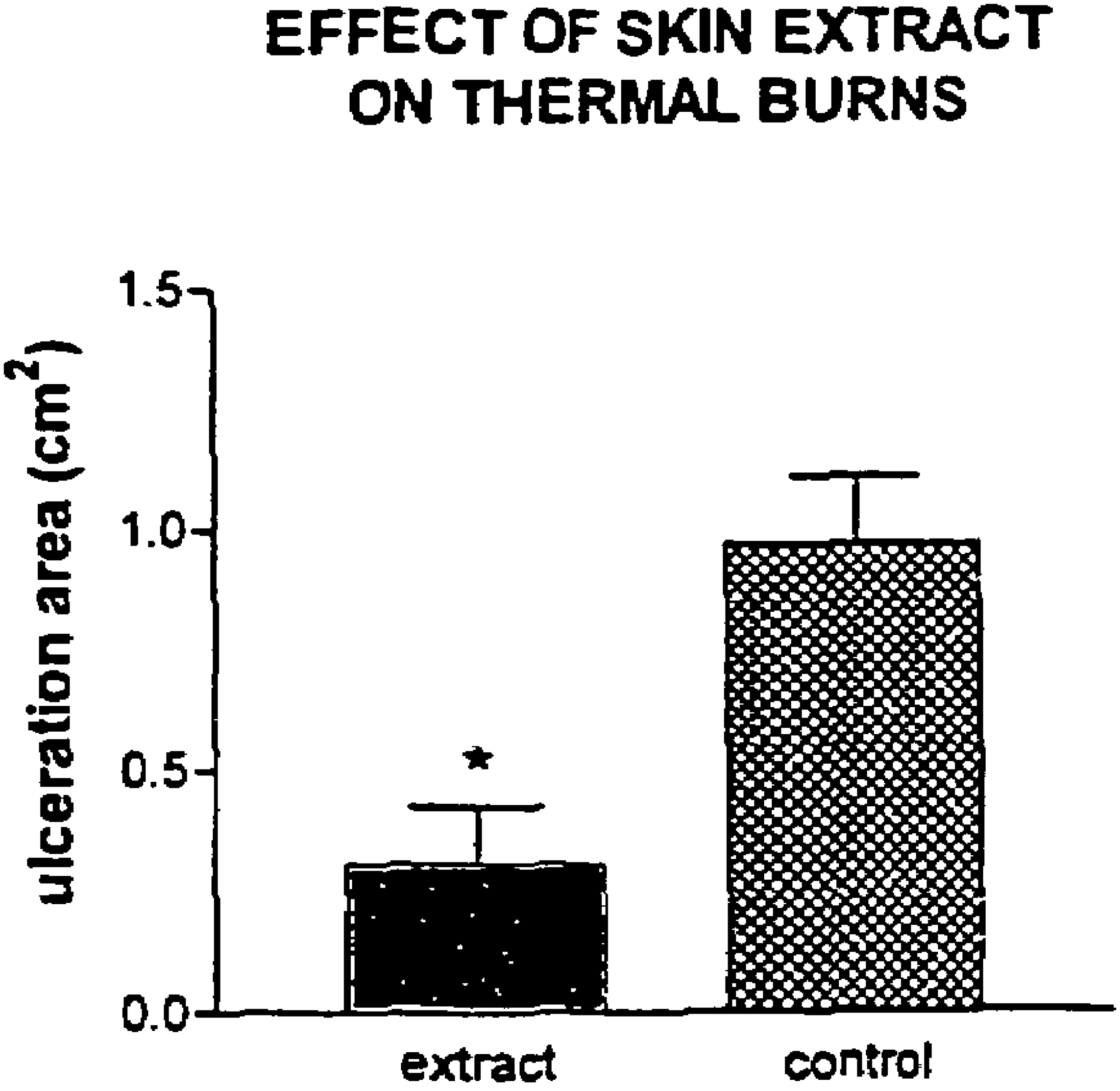
FIG. 1 shows the protective effect of the skin extract against thermal skin burns.

FIG. 1 demonstrates the protective effect of the extract against thermal burns. In the animal group treated with the extract there was a statistically significant reduction of 68% in the ulceration area as compared to the control animals injected with saline.

It was postulated that topical treatment of thermal or chemical skin burn with iodine preparation, produces factors which protects the tissue against burns. The present invention now identifies peptide factors that are isolated from the skin after exposure to thermal or chemical injury followed by treatment with iodine. These peptides have been identified, prepared synthetically in substantially pure form, and shown to confer their protective effects on the skin of naïve animals.

The present invention relates to protection by the factors against inflammation and inflammatory processes including but not limited to skin burns. Bums relate to tissue damage caused by heat stimuli, cold stimuli, chemical stimuli, electric stimuli, ultraviolet irradiation, ionizing and non-ionizing irradiation, irradiation of all kinds including electromagnetic and ultrasound.

Histone H2A fragment 36–44 (peptide III and its derivatives including the derivatives of the peptide 3 series), are species dependent sequences, and related sequences, especially human homologues are explicitly included in the scope of the invention. All active analogs of these sequences are also within the scope of the invention. Active analogs may encompass many variants as arc well known in the art, including but not limited to truncations or extensions of amino acids at the amino terminus or carboxy terminus, insertion or deletion of amino acids, N-methylated analogs, and other modifications, provided that these analogs possess anti-inflammatory properties.

The anti-inflammatory properties of Fibrinopeptide A (peptide IV and its derivatives), are also species dependent sequence, and related sequences especially human homologues are explicitly included in the scope of the invention. All active analogs of these sequences are also within the scope of the invention. Active analogs may encompass many variants as are well known in the art, including but not limited to truncations or extensions of amino acids at the amino terminus or carboxy terminus, insertion or deletion of amino acids, N-methylated analogs, and other modifications, provided that these analogs possess anti-inflammatory properties It is now disclosed that unexpectedly the anti-inflammatory activity of the fibrinopeptide A fragments are synergistically enhanced when given together with another anti-inflammatory peptide of the present invention, e.g., peptide 3m 1, or with other known anti-inflammatory agents, e.g., anti TNF alpha antibodies and anti IL1 antibodies.

The term "noxious stimuli" as used herein and in the claims is intended to encompass any trauma or insult or disease or condition involving an inflammatory response. since the toxicity of SM results from inflammatory response and involvement of inflammatory mediators, namely, induction, synthesis, activation, secretion are involved in the evolution and creation of tissue damage caused by noxious stimuli (thermal, chemical, irradiation, etc.). Since the peptides have proven to be particularly efficacious against skin burns, they were also tested and demonstrated to act as bona fide anti-inflammatory agents.

As novel anti-inflammatory agents, the peptides are expected to be efficacious in all diseases or disorders that involve inflammation or inflammatory activity. Therefore, this invention relates to the protective effect of the H2A histone 36–44 fragment and its analogs, and fibrinopeptide A against all disorders or diseases that are related to or involve inflammatory process (whether alone or together as with additional known anti-inflammatory agents, including but not limited to TNF and IL1 antibodies). These include, but are not limited to inflammatory processes related to diseases, e.g., psoriasis, arthritis, Crohn's disease, degenerative diseases such as muscle dystrophy, multiple sclerosis, Parkinson's disease, amyotrophic lateral sclerosis, Alzheimer disease, sepsis, malignant and non-malignant rumors; as well as chemical-, heat- and irradiation-induced inflammatory responses.

Fibrinopeptide A is known to have anti-inflammatory properties (Ruhenstroth-Bauer G et al., Inflammation 5, 343–351, 1981) but its combination with histone H2A fragment, anti TNF antibodies and anti IL1 antibodies, resulting in significant anti-inflammatory, is novel. The histone H2A peptide fragment having residue numbers 36–44 is novel, and its anti-inflammatory properties are also novel. Smaller fragments of these peptides or other analogs are also claimed. In our experimental system, namely the mouse ear edema test, fibrinopeptide A had weak anti-inflammatory effect, however, its combination with the histone H2A fragment and anti TNF antibodies and anti IL1 antibodies, gives a novel synergistic effect.

Protection can be achieved by prophylactic treatment, i.e. treatment with the factor (5 minutes to 3 days) prior to the noxious stimuli protects the individual against burns. Protection can also be achieved by post-exposure treatment with the factor.

The dose for administration will be determined in accordance with the condition to be treated. Therapeutic doses are defined as the range of doses able to induce a statistically significant reduction in damage compared with that suffered by an individual not receiving treatment with the protective factor. Protection against noxious stimuli may also manifest itself in terms of decreased toxicity as expressed by secondary criteria, as are well known in the art, including reduction in weight loss suffered after exposure to noxious chemicals, or in terms of maintenance of food consumption.

The extent of tissue protection will also be influenced by the general health conditions of the subject to be treated, which will relate to various factors including but not limited to the pre-existence of any underlying pathology, as well age and other factors.

The route of administration will depend on the condition that it is intended to treat with the factor. Suitable routes of administration include but are not limited to parenteral injections, e.g., intradermal, intravenous, intramuscular, intralesional, subcutaneous, intrathecal, and any other mode of injection as is known in the art. Although the bioavailability of peptides administered by other routes may be lower than when administered via parenteral injection, by using appropriate formulations it is envisaged that it will be possible to administer the compositions of the invention via transdermal, oral, rectal, topical, nasal, inhalation and ocular modes of treatment with the factor.

The term "pharmaceutical composition" relates to any pharmaceutically acceptable formulation of the factors of the invention comprising at least one diluent or excipient, as is well known in the art. This term is understood to encompass aqueous solutions, cosolvent solutions, dry powders for solution, solid formulations, formulations for inhalation, suppositories, sustained release formulations, gels, lotions, creams, emulsions, liposomes and the like. In addition to the active ingredient of the invention the formulation may further comprise isotonicity agents, preservatives, buffers cryoprotectants and the like as is well known in the art. It is further understood that the factors of the invention may be formulated or administered together with additional active ingredients as may be required to treat the condition of the patient.

The term "modified peptide" or "peptide analog" may be used herein interchangeably, and relate to a peptide that undergoes chemical modification for stabilization against proteolytic and other degradative activities and/or physical or chemical activities. Modified peptides include, but are not limited to, N-methylation of one or several peptide bonds, retro-inverso modification of one or several peptide bonds, substitutions of amino acids by conservative replacements such as are known in the art, addition or omission of amino-terminal or carboxy-terminal amino acids.

Thus, for example, introduction of proline to the amino terminus may confer resistance against aminopeptidases, while amidation of the carboxy terminus to produce carboxamide may confer resistance against carbox),peptidases.

Replacement of similar amino acids such as isoleucine with leucine or valine, glutamate with aspartate, tyrosine with phenylalanine is considered as homologous peptides.

The term "protection" relates to reduction of degree of lesion as measured by gross pathology or histopathological evaluation, subjective burning sensation or other accepted parameters for tissue damage, lesion, discomfort and pain.

Tissues that can be protected extends to all kinds of tissues or cells in the body including skin and all skin lavers, subcutaneous tissues, muscles, mucosal membranes, neuronal tissue, lungs, upper and lower airways, eyes, gastrointestinal tract, urinary tract, bones and bone marrow.

The protective factor can be used for accelerated healing of and prevention of development of wounds including decubitus, ulcers (also induced by drugs), internal and external wounds, abscesses and various bleedings.

The protective factors may be used for protection of bone marrow, intestinal epithelium, hair follicles and other sensitive tissues against chemotherapeutic agents such as anticancer drugs, immunosuppresive agents, irradiation and other noxious stimuli.

The protective factors may be used for treatment and protection on the central and peripheral nervous systems against noxious stimuli caused by, but not limited to, chemicals, drugs, all kinds of irradiation and mechanical stress. As neuronal-affecting agents the factors may also serve in treatment of a variety of mental diseases and mental-related syndromes.

The protective factors may also be used for treatment or prevention of tissue damage including, but not limited to, neuronal, neurological, hepatic, nephrologic, urologic, cardiac, pulmonary, gastrointestinal, visual, audiologic, spleen, bone, bone marrow and muscular defects. Treatment or prevention of tissue damage may be accomplished in the fetus, newborn, child, adolescent as well as in adults and old persons, whether the condition or disorder to be treated is spontaneous, of traumatic etiology, as a congenital defect or as a teratogenic phenomenon.

The protective factors may be used for treatment or prevention of diseases or syndromes related to, or involving inflammatory processes or inflammatory mediators.

According to the currently most preferred embodiment of the invention the term "protective factors" relates to the materials, which elute under the specific chromatography conditions exemplified hereinbelow at 22–27 min retention time. The currently preferred factors are peptides III, IV, VI, VII and all of their analogs, variants and derivatives. "Protective factors" relates to all of these peptides each as a single compound and/or all possible combinations of two or more of these peptides including modified peptides.

The following examples demonstrate the invention described above but it is not intended to limit the scope thereof in any way.

EXAMPLES

I. Exemplary Protocol for Obtaining Extract and Identifying Active Peptides

In order to isolate the protective factor, the animals were exposed to trauma using the following protocol: A guinea pig was shaved (electrical shaver) twenty-four hours prior the experiment. Wells were constructed on the back of the anesthetized (induced by 15–30 mg/kg pentobarbital ip) animal by the following procedure [Wormser U et al. (1997) Arch. Dermatol. Res. 289, 686–691]. A plastic tube cover (inner diameter of 1.7 cm) was cut to form an open-ended cylindrical well, and a thin layer of commercial silicon sealing ointment was applied to one edge of the well. The well was then attached to the animal back, and tested to ensure that liquid inside the well did not leak out. The skin area covered by the well was 1.13 sq. cm. Eight such wells were constructed on the back of each guinea pig. Maintenance of anesthesia during the experiment was achieved by 15 mg/kg pentobarbital ip. Each area inside the well was exposed, for 5 seconds, to the base (1.2 cm diameter) of a glass beaker (4.5 cm height) containing 90° C. water.

Topical application of the fresh liquid obtained from squeezing cut leaf of Aloe vera was shown to protect guinea pigs against thermal burns. Thus, a part of the following experiments was carried out with the Aloe Vera liquid instead the povidone-iodine or iodine ointment as a protectant.

Immediately thereafter, fresh Aloe Vera liquid obtained by squeezing cut Aloe Vera leaf was applied to cover the entire area of the skin. In several experiments the Aloe Vera was replaced by 10% povidone iodine solution or by 2% iodine tincture. Alternatively, the anesthetized animal was exposed to a preheated (75° C.) metal (3×5 cm) for 5 sec. Then iodine tincture was applied every 10–15 minutes (to keep continuous contact with iodine solution).

After two hours the liquid was washed out with water, and the skin was gently dried with a filter paper. The animal was sacrificed, the treated skin was removed from the animal, put on a glass petri dish (9 cm diameter), and sliced into pieces of about 2×2×2 mm. The slices were extracted with 40 ml ethanol containing 800 μl acetic acid in a 260 ml plastic tissue culture flask incubated vertically at 37° C. for 1 hour and mixed with magnetic stirrer. Later on it was found that incubation at 4° C. for 1 hour might give better results. The extract was evaporated by rotary evaporator and Speed Vac to a final volume of 100 μl.

The extract was diluted with 2% acetonitril/0.08% trifluoroacetic acid in double distilled water (solvent A of high performance liquid chromatography (HPLC) gradient system). The tubes were centrifuged (7 min×15,000 g), filtered with 2 μm filter, and subjected (50 μl) to HPLC (Applied Biosystem equipped with 140 B solvent delivery system and 1000 S diode array detector) using Vydac C18 column (2.1×250 mm) and C18 precolumn. Each purification was performed. under the following gradient: during the first 2 min an isocratic run with 2% solvent B (acetonitril containing 0.1% trifluoroacetic acid, and 2% double distilled water), then a gradient of 2% to 42% of solvent B during 42 min (flow rate 150 μl/min). For washing and re-equilibration the following system was used: a gradient from 42% to 95% of solvent B during the next 5.8 min (flow rate 300 μl/min), then an isocratic run at 95% solvent B during the next 4.2 min (flow rate 300 μl/min), and finally a 2% solvent B (flow rate 150 μl/min).

The fraction eluted at 25 min (about 25% of solvent B) was diluted 1:1 in concentrated (x2) phosphate buffered saline (PBS) to give a mixture of physiologic PBS concentration and factor (together with trifluoroacetic acid and acetonitril). Surprisingly the two latter components neither affected the protective effect of the factor nor the effect of the noxious stimuli).

Identification of the factors by HPLC/MS/MS and by sequence analysis revealed four peptides with the following sequence:

```
H-Lys-Gly-Asn-Tyr-Ala-Glu-Arg-Ileu-Ala-OH
(peptide III; SEQ ID NO:1)

H-Thr-Thr-Asp-Thr-Glu-Phe-Glu-Ala-Ala-Gly-Gly-Gly-
Val-Arg-OH (peptide VII; SEQ ID NO:4)

H-Thr-Asp-Thr-Glu-Phe-Glu-Ala-Ala-Gly-Gly-Gly-Val-
Arg-OH (peptide VI; SEQ ID NO:3)

H-Asp-Thr-Glu-Phe-Glu-Ala-Ala-Gly-Gly-Gly-Val-Arg-
OH (peptide IV; SEQ ID NO:2)
```

Peptide III was found to be a partial sequence of Histone H2A that its carboxy terminal Gly was substituted by Ala. Peptide VI was identified as guinea pig fibrinopeptide A, while peptides IV and VII differ from peptide VI by omission and addition, respectively, of the amino terminal threonine moiety.

Peptides and their analogs were synthesized by peptide synthesizer in the Inter Departmental Unit, Institute of Life Sciences, Faculty of Sciences, The Hebrew University.

II. Overview of the Protective Effects of Extracts and Peptides

A) Prophylactic treatment with skin extract reduced ulceration area of heat-induced skin lesions.

As demonstrated in Example 1 intradermal injections of skin extract 1–5 min before heat stimulus (exposure of guinea pig skin to 75° C. for 10 sec) caused reduction of 69% in ulceration area as compared to the control animals (injected with saline only).

B) Prophylactic treatment with isolated HPLC fraction reduced skin damage caused by thermal and chemical stimuli.

It was found that prophylactic intradermnal injections of the fractions eluted at retention time of 22–27 min. reduced the degree of thermal and chemical (mechlorethamine-induced) skin injuries (Example 2).

C) Prophylactic intradernial injections of combination of peptides III, IV, VI, VII and cocktail of proteinase inhibitors (to prevent peptide degradation) reduced skin ulceration area induced by thermal stimuli (76% reduction) and chenmical stimulus (45% reduction) caused by sulfur mustard (example 3).

D) Prophylactic intradermnal injections of peptide III and cocktail of proteinase inhibitors (to prevent peptide degradation) reduced (by 67%) ulceration area of skin exposed to chemical (sulfur mustard-induced) stimuli (Example 4).

E) Prophylactic intradermal injections of peptide III and cocktail of proteinase inhibitors (to prevent peptide degradation) reduced (by 95%) ulceration area of skin exposed to thermal stimuli (Example 5).

F) Prophylactic intradermal injections of peptide IV and cocktail of proteinase inhibitors (to prevent peptide degradation) reduced (by 62%) ulceration area of skin exposed to chemical (sulfur mustard-induced) stimuli (Example 4).

G) Prophylactic intradernal injections of peptide VI and cocktail of proteinase inhibitors (to prevent peptide degradation) reduced (by 42%) ulceration area of skin exposed to chemical (sulfur mustard-induced) stimuli (Example 4).

H) Prophylactic intradermal injections of peptide VII and cocktail of proteinase inhibitors (to prevent peptide degradation) reduced (by 35%) ulceration area of skin exposed to chemical (sulfur mustard-induced) stimuli (Example 4).

I) Prophylactic intradermal injections of peptide VII and cocktail of proteinase inhibitors (to prevent peptide degradation) reduced by (83%) ulceration area of skin exposed to thermal stimuli (Example 5).

J) Prophylactic intradermal injections of combination of peptides III, IV, VI, VII and cocktail of proteinase inhibitors (to prevent peptide degradation) protected the guinea pigs against loss of body weight associated with chemical stimulus caused by exposure to sulfur mustard. Example 6 shows 10.9% increase in body weight in peptide combined with proteinase inhibitors-treated animals while treatment with proteinase inhibitors only increased body weight by 6.8%.

K) Prophylactic intradermal injections of cocktail of proteinase inhibitors reduced (by 22%) ulceration area of skin exposed to chemical (sulfur mustard-induced) stimuli (Example 4).

L) Prophylactic intradermal injections of cocktail of proteinase inhibitors reduced (by 75%) ulceration area of skin exposed to thermal stimuli (Example 5).

M) Prophylactic intradermal injection of the mono N-methyl analog, $MeAla^5$-peptide III; 5 min prior exposure, caused statistically significant reduction of 80% in mustard gas-induced ulceration area as compared to the control group.

N) Prophylactic intradermal injection of the mono N-methyl analog, $MeIleu^8$-peptide III, 5 min prior exposure, caused statistically significant reduction of 72% in mustard gas-induced ulceration area as compared to the control group.

O) Prophylactic intradermal injection of the mono N-methyl analog-$MeGly^2$-peptide III, the di N-methyl analog-$MeGly^2$, $MeIleu^8$-peptide III, and the tri N-methyl analog-$MeGly^2$, $MeAla^5$, $MeIleu^8$-peptide III, 5 min prior exposure, caused reduction of 39%, 31% and 0%, respectively, in mustard gas-induced ulceration area as compared to the control group. It might be hypothesized that that substitution of $Gly^2$ moiety by its N-methyl analog, N-methyl-Gly, reduces the protective activity of the peptide.

P) Prophylactic intravenous injection of peptides IV and 3b into mice reduced the inflammatory response caused by sulfur mustard (SM). Peptide IV and 3b (40 mg/kg) reduced the inflammatory response by 19% and 18%, respectively.

Q) Prophylactic intravenous injection of the combination of anti mouse IL1 beta antibodies, anti mouse TNF alpha antibodies, peptide IV and peptide 3m 1 reduced the SM-induced inflammatory response as expressed by mouse ear swelling. This combination reduced SM-induced ear swelling by 31%. Omission of peptide FV from this combination reduced mouse swelling by 15%. Peptide IV only has no protective effect. Thus, peptide IV had synergistic effect on the protection by the combination of anti mouse IL1 beta antibodies, anti mouse TNF alpha antibodies, and peptide 3m1.

Example 1

Protective Effect of Extract Against Thermal Burns

Backs of haired guinea pigs (male, Duncan Hartley, 650–850 g) were shafed 24 hours prior the experiment. The animals were anesthetized by 30 mg/kg pentobarbital sodium ip. Backs were cleaned with wet soft white paper and let to dry out before the beginning of experiment. Eight sites (four on each side) of each back were exposed to heat by the following procedure. A plastic tube cover (inner diameter of 1.7 cm) was cut to form open-ended cylindrical well and a thin layer of commercial silicon sealing ointment was applied to one edge of the well. The well was then attached to the animal back so liquid inside the well did not leak out. Each well was exposed to 1 ml 75° C. distilled water for 10 sec. Immediately after sucking out the hot water, iodine (1 ml, 2% in tetraglycol) was applied into the well for 2 hours. In the end of procedure the iodine was sucked out and the treated skin sites of 4 guinea pigs were removed, cut into small pieces and extracted in 100 ml ethyl alcohol in ultrasonic bath at 37° C. for 1 hour.

The skin extract was concentrated to a volume of 20–40 μl, diluted in 800 μl saline (0.9% NaCl), and injected intradermally into guinea pigs. Each guinea pig received 4 injections (50 μl each at 4 sites, two at each side of the back) 5 min before the heat stimulus (75° C. water for 10 seconds) by the well system. Additional control guinea pigs were injected with saline, and exposed to heat in the same manner. The animals were daily checked for gross pathology. Ulceration area was measured by digital camera equipped with a ruler. Results are expressed as mean ±SEM of 18 extract-injected sites and 18 saline-injected sites (control) using the Mann-Whitney (two-tailed) for statistical evaluation of the differences between the groups. *P<0.05

As demonstrated in FIG. 1, intradermal injection of a skin extract into guinea pig skin 5 min before the heat stimulus reduced the ulceration area by 69% as compared to the control animals (injected with saline only).

Example 2

Protective Effect of Isolated HPLC Fraction

Intradermal injection of the factor (purified by HPLC from the skin extract) into guinea pigs that were exposed to heat (75° C. for 20 sec on a circle of 0.5 cm diameter), or to chemical (500 μg/0.7×0.7 cm mechlorethamine hydrochloride) stimuli was evaluated for gross pathology after 3 days. The injection sites were located 1 cm from the edge of the application site. A control guinea pig was injected with an HPLC fraction eluted at the same retention time (25 min), but without the factor. The degree of lesion was evaluated as follows: 0 no damage, 1 slight erythema, 2 strong erythema, 3 small ulceration (0.1×0.1 cm), 4 moderate ulceration (0.2×0.2 cm), 5 strong ulceration (0.3–0.4×0.3–0.4 cm). Numbers shown in table 1 indicate the severity of lesions whereas numbers in parentheses (n=) indicate number of application sites in which the indicated degree of lesion was demonstrated. As shown in Table 1, injection of the factor protected the guinea pigs against heat or chemical stimuli, i.e., the skin injuries were significantly reduced. In contrast, the skin of the control guinea pigs was markedly damaged by the noxious stimuli.

TABLE 1

HPLC fraction-induced protection against thermal and chemical stimulation in the guinea pig skin model.

| | lesion | |
|---|---|---|
| animal | thermal | chemical |
| treated | 0 (n = 14)<br>1 (n = 4) | 1 (n = 4) |
| control | 3 (n = 8)<br>4 (n = 5)<br>5 (n = 3) | 5 (n = 4) |

It can be demonstrated that injection of the factor protected guinea pigs against heat and chemical (mechlorethamine hydrochloride) stimuli. It is shown that both the chemical and thermal injuries slightly affected the skin when the animal was intradermally injected with the factor before the stimuli whereas the controls were markedly damaged by the noxious stimuli. It is noteworthy that protection was also achieved at sites not adjacent to injection sites, indicating the systemic (and not only local) effect of the injected factor.

Example 3

Protective Effect of Combination of Peptides III, IV, VI, VII Against Thermal and Chemical Burns Backs of haired guinea pigs (male, Duncan Hartley, 650-850 g) were shaved 24 hours prior the experiment. The animals were anesthetized by 30 mg/kg pentobarbital sodium ip. Backs were cleaned with wet soft white paper and let to dry out before the beginning of experiment. Out of six sites of each animal three were exposed to 1 μl Sulfur mustard (SM) and three to heat by the following procedure. A plastic tube cover (inner diameter of 1.7 cm) was cut to form open-ended cylindrical well and a thin layer of commercial silicon sealing ointment was applied to one edge of the well. The well was then attached to the animal back so liquid inside the well did not leak out. Each well was exposed to 1 ml 75° C. distilled water for 10 sec, then water was sucked out and well was removed. Five min prior to exposure each guinea pig received 4 intradermal injections (50 μl each, total volume of 200 μl per animal) located about 1.5 cm laterally to two adjacent exposure sites. Each injection contained the following components:

A) Hydrophobic proteinase inhibitors: Pepstatin A and Chymostatin, 1 mg of each inhibitor was dissolved in 1 ml dimethylsulfoxide (DMSO);

B) N-Acetyl-Leu-Leu-Methioninyl; 1 mg of each inhibitor was dissolved in 1 ml dimethylsulfoxide (DMSO);

C) Antipain, Leupeptin, p-Aminobenzoyl-Gly-Pro-D-Leu-D-Ala Hydroxamic Acid of SEQ ID NO:15, Elastaminal, phophoramidon, Bestatin, N-CBZ-PRO-Leu-Gly-Hydroxamate and Puromycin-dihydrochloride; 1 mg of each inhibitor was dissolved in 100 μl 0.9% NaCl;

D) Solution for injection: One ml solution for intradermal injection contained 100 μL solution C, 5 μl solution A, 5 μsolution B, 200 μl 0.9% NaCl and 800 μl containing 5 mg of each of the following peptides III, VI, VII and 2.1 mg of peptide IV.

E) Control solution (C in graph means control, n=30): The control guinea pigs were similarly injected (4 injections of 50 μl each) with NaCl 0.9% containing 1% DMSO.

The animals were daily checked for gross pathology, Ulceration area was measured by digital camera with the aid of a ruler. Results are expressed as mean ±SEM (each column represents 12 exposure sites) using the Mann-Whitney (two-tailed) for statistical evaluation of the differences between the groups.

Figure 2:
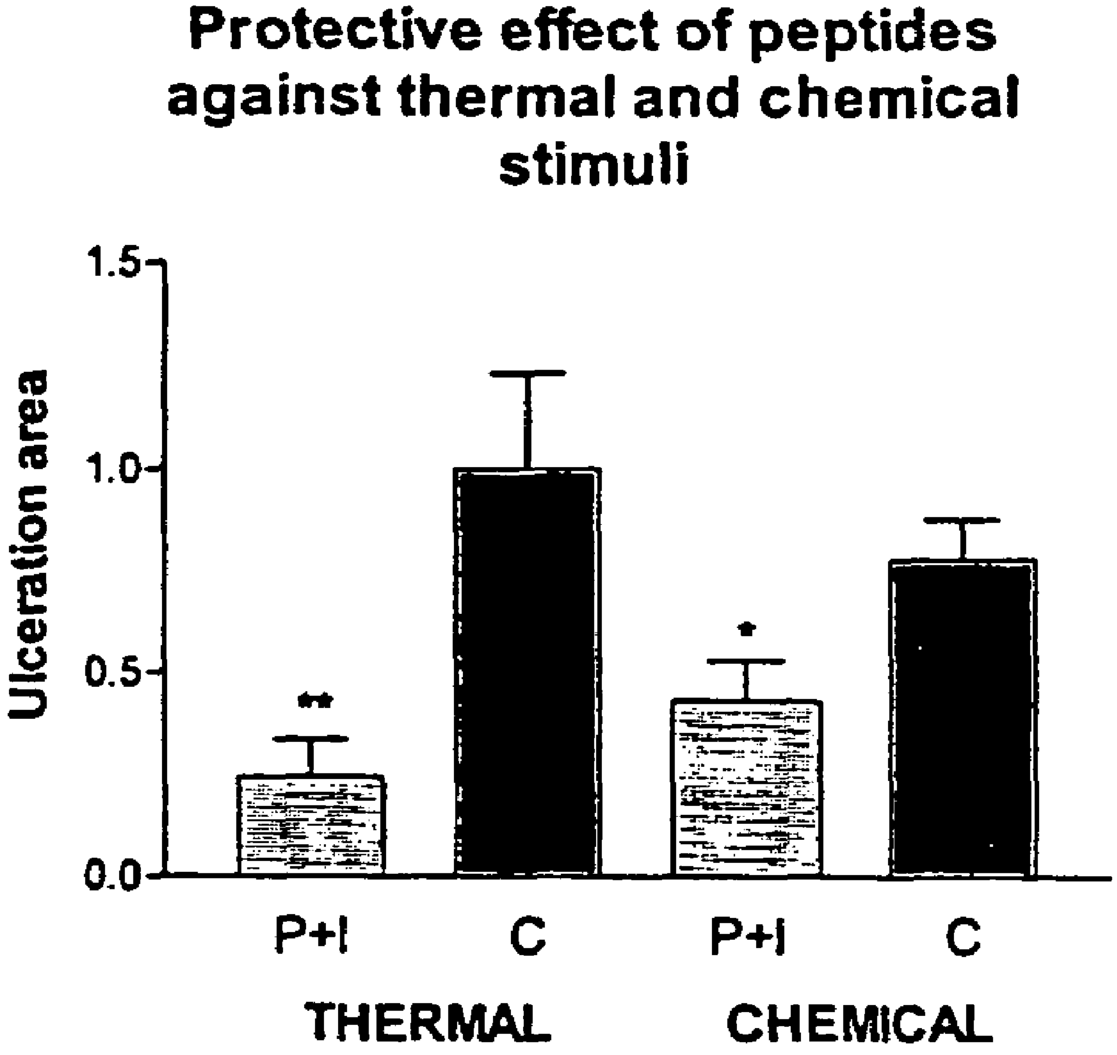
FIG. 2 shows the protective effect of the mixture of peptides III, IV, VI, and VII against thermal or chemical skin burns.

As shown in FIG. 2 there is a significant reduction in the damage induced by either thermal or chemical burns after administration of the peptides together with the protease inhibitors, (* $p<0.05$; ** $p<0.02$).

Example 4

Protective Effect of Peptides Against Chemical Skin Burns

Backs of haired guinea pigs (male, Duncan Hartley, 650–850 g) were shaved 24 hours prior the experiment The animals were anesthetized by 30 mg/k pentobarbital sodium ip. Backs were cleaned with wet soft white paper and let to dry out before the beginning of experiment. Out of six sites of each animal three were exposed to 1 µl Sulfur mustard (SM) and three to heat by the following procedure. A plastic tube cover (inner diameter of 1.7 cm) was cut to form open-ended cylindrical well and a thin layer of commercial silicon sealing ointment was applied to one edge of the well. The well was then attached to the animal back so liquid inside the well did not leak out. Each well was exposed to 1 ml 75° C. distilled water for 10 sec, then water was sucked out and well was removed. Five min prior to exposure each guinea pig received 4 intradermal injections (50 µl each, total volume of 200 µl per animal) located about 1.5 cm laterally to two adjacent exposure sites. Each injection contained the following components:

A) 1 mg Pepstatin and 1 mg Chymostatin were dissolved in 1 ml DMSO and sonicated for 5 min;

B) 1 mg Antipain and 1 mg Leupeptin were dissolved in 1 ml 0.9% NaCl followed by addition of 5 µl solution A.

C) Petide solution for injection: 4 tubes containing solution B were prepared. Each tube contained 5 mg peptide of one sort, so that each tube contained all kinds of inhibitors and one kind of peptide. Each peptide is indicated by its Roman numerals plus I (inhibitors of proteinases) (n=9). Additional experiment in which a mixture of all four peptides (III, IV, VI, VII), 5 mg each, were dissolved in 1 ml solution B, and were injected to the guinea pigs is indicated as PI-peptides and inhibitors (n=21).

D) Inhibitor solution for injection: 1 ml solution B containing 5 µl solution B (indicated as 1) (n=9).

E) Control solution for injection: 1 ml 0.9% NaCl containing 5 µl DMSO (indicated as C) (n=30).

The animals were daily checked for gross pathology, Ulceration area was measured by digital camera with the aid of a ruler. Results are expressed as mean ±SEM using the Mann-Whitney (two-tailed) for statistical evaluation of the differences between the groups.

Figure 3:
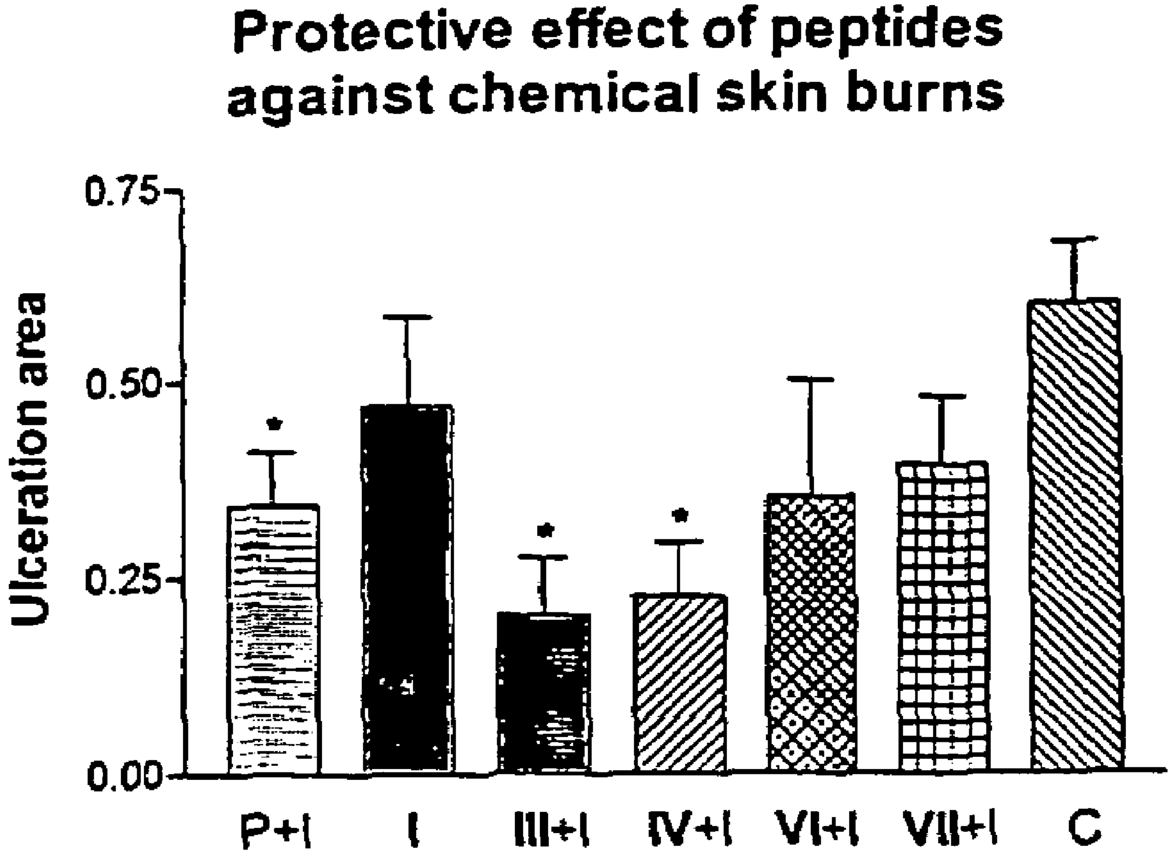
FIG. 3 depicts the protective effect of each of the peptides III, IV, VI, or VII against chemical skin burns.

As can be seen from FIG. 3 the treatment of chemical burns with Peptides III and IV were each significantly improved over controls, as were the mixture of all four of the peptides. An asterisk denotes statistical significance at the level of $p<0.05$.

Example 5

Protective Effect of Peptides Against Thermal Skin Burns

Backs of haired guinea pigs (male, Duncan Hartley, 650–850 g) were shaved 24 hours prior the experiment The animals were anesthetized by 30 mg/kg pentobarbital sodium ip. Backs were cleaned with wet soft white paper and let to dry out before the beginning of experiment. Out of six sites of each animal three were exposed to 1 µl Sulfur mustard (SM) and three to heat by the following procedure. A plastic tube cover (inner diameter of 1.7 cm) was cut to form open-ended cylindrical well and a thin layer of commercial silicon sealing ointment was applied to one edge of the well. The well was then attached to the animal back so liquid inside the well did not leak out. Each well was exposed to 1 ml 75° C. distilled water for 10 sec, then water was sucked out and well was removed. Five min prior to exposure each guinea pig received 4 intradermnal injections (50 µl each, total volume of 200 µl per animal) located about 1.5 cm laterally to two adjacent exposure sites. Each injection contained the following components:

F) 1 mg Pepstatin and 1 mg Chymostatin were dissolved in 1 ml DMSO and sonicated for 5 min;

G) 1 mg Antipain and 1 mg Leupeptin were dissolved in 1 m1 0.9% NaCl followed by addition of 5 µl solution A.

H) Peptide solution for injection: 4 tubes containing solution B were prepared. Each tube contained 5 mg peptide of one sort, so that each tube contained all kinds of inhibitors and one kind of peptide. Each peptide is indicated by its Roman numeral plus I (inhibitors of proteinases) (n=9). Additional experiment in which a mixture of all four peptides (III, IV, VI, VII), 5 mg each, were dissolved in 1 ml solution B, and were injected to the guinea pigs (indicated as PI-peptides and inhibitors) (n=21).

I) Inhibitor solution for injection: 1 ml solution B containing 5 µl solution B (indicated as I) (n=9).

J) Control solution for injection: 1 ml 0.9% NaCl containing 5 µl DMSO (indicated as C) (n=30).

The animals were daily checked for gross pathology, Ulceration area was measured by digital camera with the aid of a ruler. Results are expressed as mean ±SEM using the Mann-Whitney (two-tailed) for statistical evaluation of the differences between the groups.

Figure 4:
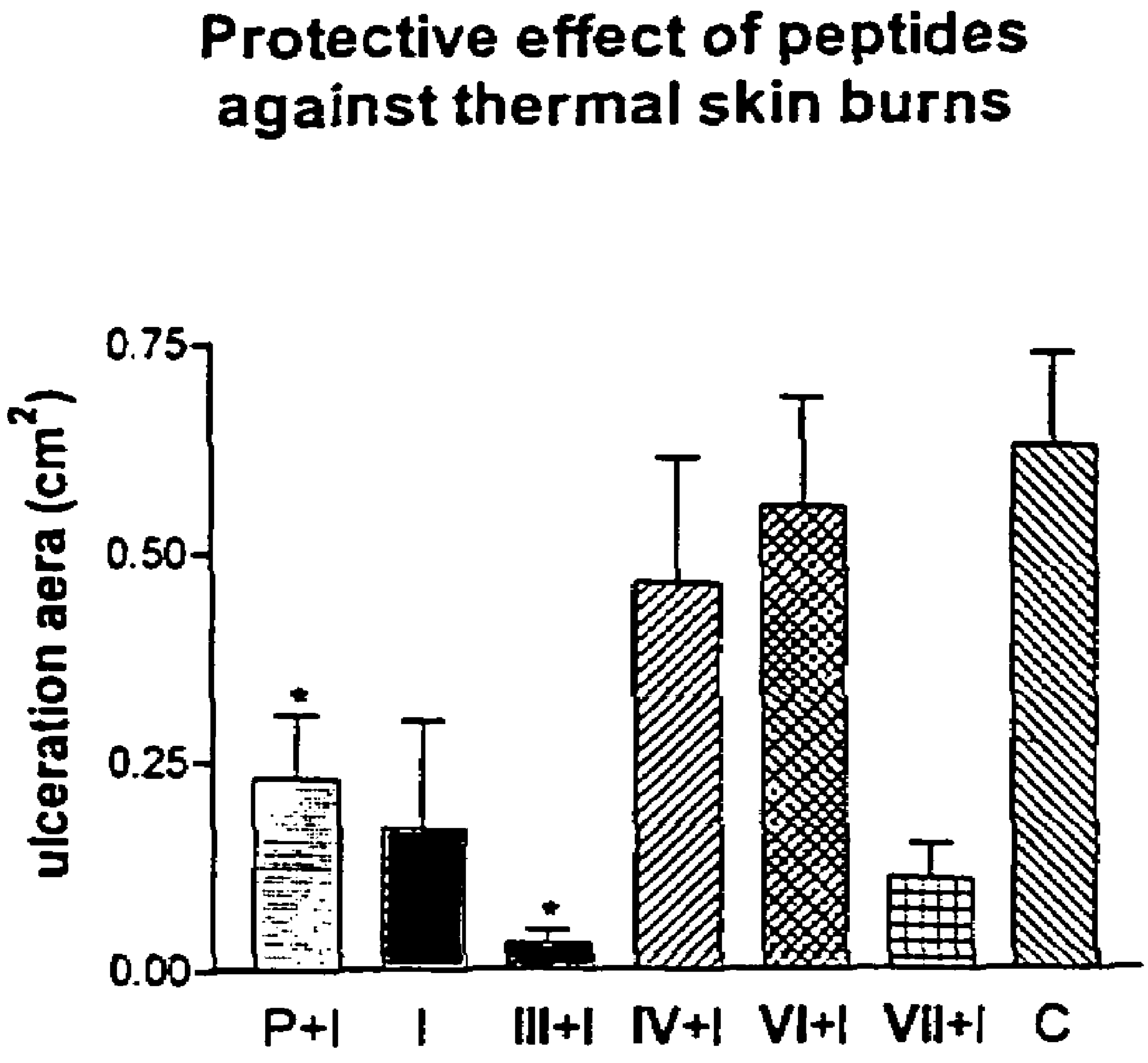
FIG. 4 depicts the protective effect of each of the peptides III, IV, VI, or VII against thermal skin burns.

As can be seen from FIG. 4 the treatment of thermal burns with Peptide III was significantly improved over controls, as were the mixture of all four of the peptides. An asterisk denotes statistical significance between the experimental group and the control group at the level of $p<0.05$.

Example 6

Effect of Peptides Against Body Weight Loss Induced by Sulfur Mustard and Thermal Injury Backs of haired guinea pigs (male, Duncan Hartley, 650–850 g) were shaved 24 hours prior the experiment. The animals were anesthetized by 30 mg/kg pentobarbital sodium ip. Backs were cleaned with wet soft white paper and let to dry out before the beginning of experiment. Out of six sites of each animal three were exposed to 1 µl Sulfur mustard (SM) and three to heat by the following procedure.

A plastic tube cover (inner diameter of 1.7 cm) was cut to form open-ended cylindrical well and a thin layer of commercial silicon sealing ointment was applied to one edge of the well. The well was then attached to the animal back so liquid inside the well did not leak out. Each well was exposed to 1 ml 75° C. distilled water for 10 sec, then water was sucked out and well was removed. Five min prior to exposure each guinea pig received 4 intradermal injections (50 μl each, total volume of 200 μl per animal) located about 1.5 cm laterally to two adjacent exposure sites. Each injection contained the following components:

A) 1 mg Pepstatin and 1 mg Chymostatin were dissolved in 1 ml DMSO and sonicated for 5 min;

B) 1 mg Antipain and 1 mg Leupeptin were dissolved in 1 ml 0.9% NaCl followed by addition of 5 μl solution A.

C) Peptide solution for injection: A mixture of all four peptides (III, IV, VI, VII), 5 mg each, dissolved in 1 ml solution B, and injected into the guinea pigs (indicated as P+I-peptides and inhibitors) (n=7).

D) Inhibitor solution for injection: 1 ml solution B containing 5 μl solution B (indicated as I) (n=3).

E) Control solution for injection: 1 ml 0.9% NaCl containing 5 μl DMSO (indicated as C) (n=7).

Animals weighed after 5 days. Results are expressed as mean ±SEM using the Mann-Whitney (two-tailed) for statistical evaluation of the differences between the groups.

Figure 5:
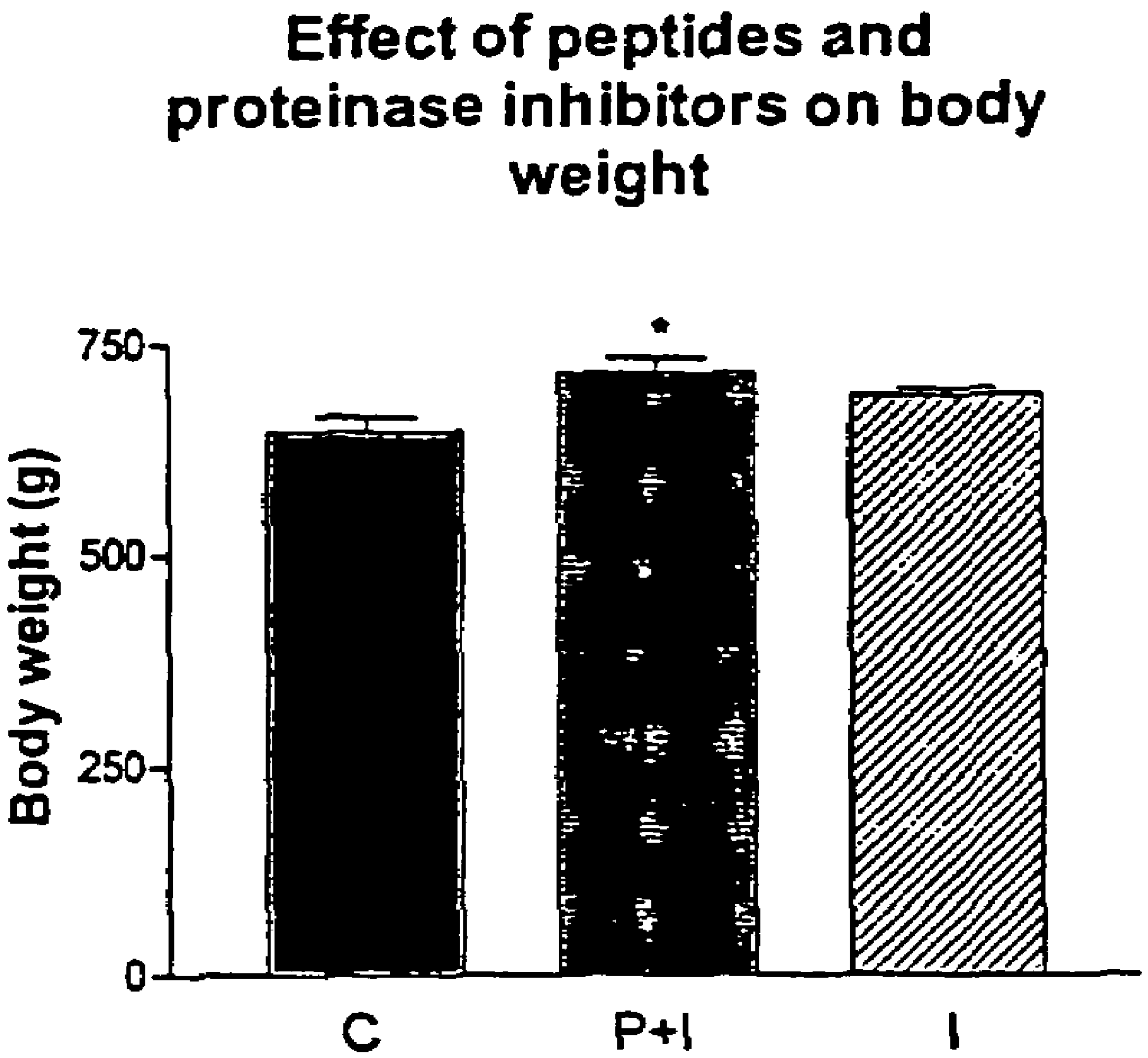
FIG. 5 shows the effect of the mixture of peptides III, IV, VI, and VII on body weight loss induced by sulfur mustard.
Figure 6:
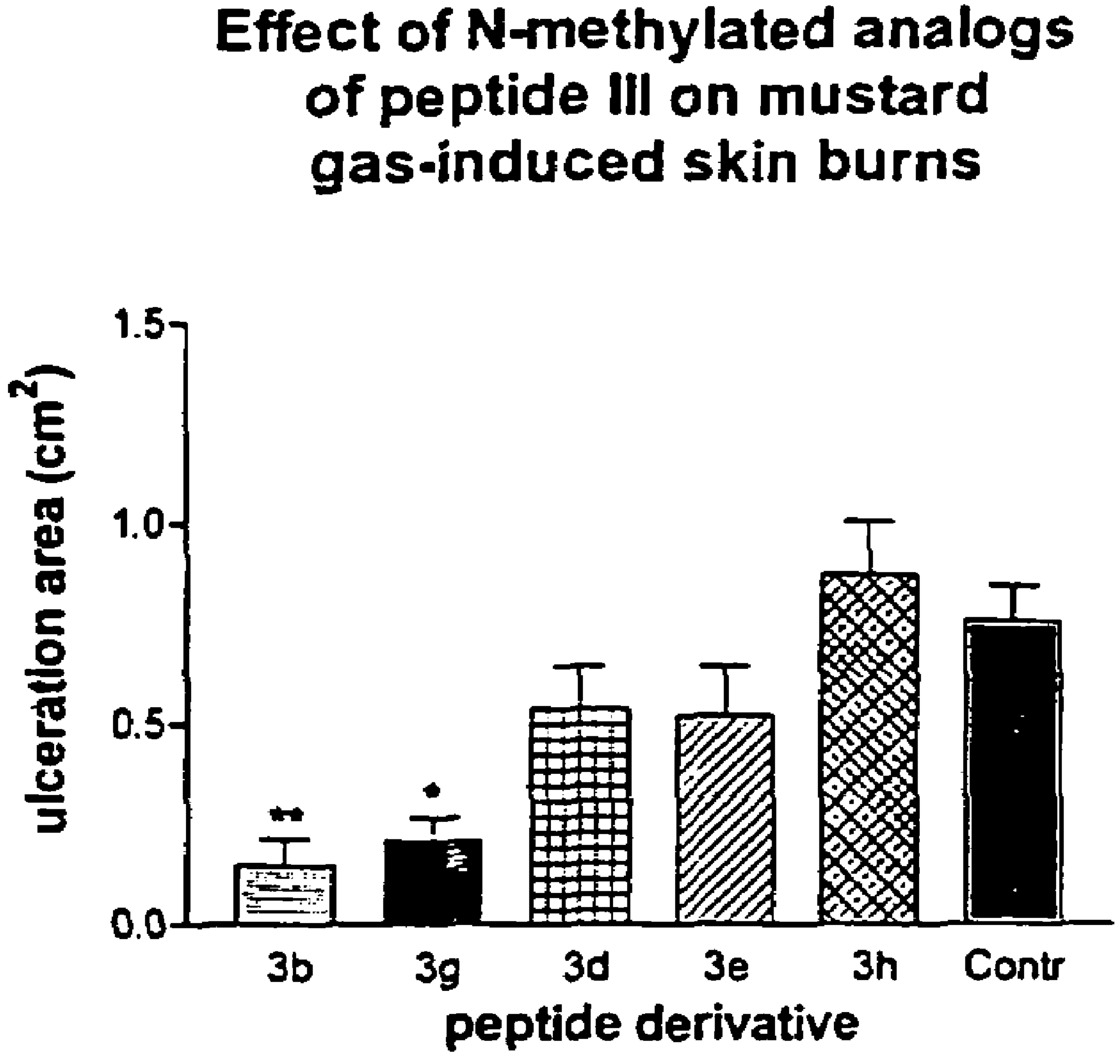
FIG. 6 shows the protective effect of N-methylated analogs of peptide III against skin burns induced by sulfur mustard.

As can be seen in FIG. 5 only the group of peptides plus inhibitors was significantly improved over controls. The asterisk denotes $p<0.05$.

The average weight of the animals was 11% higher in the peptides- and proteinase inhibitors-treated group than in the control. The proteinase inhibitors-treated group showed 6.8% elevation in the body weight, compared to the controls.

Example 7

Protective Effect of N-Methylated Analogs of Peptide III Against Mustard Gas-Induced Skin Lesions Backs of haired guinea pigs (male, Duncan Hartley, 650–850 g) were shaved 24 hours prior the experiment. The animals were anesthetized by 30 mg/kg pentobarbital sodium ip. Backs were cleaned with wet soft white paper and let to dry out before the beginning of experiment. Six sites of each animal were exposed to 1 μl Sulfur mustard (SM). Five min prior to exposure each guinea pig received 4 intradermal injections (50 μl each, total volume of 200 μl per animal) located about 1.5 cm laterally to two adjacent exposure sites. Each analog was separately tested for its ability to protect against SM. Each injection contained 50 μl solution containing 5 mg/ml analog. Each analog was examined on separate animals (i.e. each animal was injected by a single peptide analog). Control groups were injected with the vehicle (saline, 0.9% NaCl). Ulceration area was measured 3 days after treatment. The following N-methylated analogs were tested:

| # | molecular structure | % protection |
|---|---|---|
| 3b | $H\text{-}Lys^1\text{-}Gly^2\text{-}Asn^3\text{-}Tyr^4\text{-}MeAla^5\text{-}Glu^6\text{-}Arg^7\text{-}Ileu^8\text{-}Ala^9\text{-}OH$ (SEQ ID NO:5) | 80** |
| 3g | $H\text{-}Lys^1\text{-}Gly^2\text{-}Asn^3\text{-}Tyr^4\text{-}Ala^5\text{-}Glu^6\text{-}Arg^7\text{-}MeIleu^8\text{-}Ala^2\text{-}OH$ (SEQ ID NO:6) | 72* |
| 3d | $H\text{-}Lys^1\text{-}MeGly^2\text{-}Asn^3\text{-}Tyr^4\text{-}Ala^5\text{-}Glu^6\text{-}Arg^7\text{-}Ileu^8\text{-}Ala^9\text{-}OH$ (SEQ ID NO:7) | 39 |
| 3e | $H\text{-}Lys^1\text{-}MeGly^2\text{-}Asn^3\text{-}Tyr^4\text{-}Ala^5\text{-}Glu^6\text{-}Arg^7\text{-}MeIleu^8\text{-}Ala^9\text{-}OH$ (SEQ ID NO:8) | 31 |
| 3h | $H\text{-}Lys^1\text{-}MeGly^2\text{-}Asn^3\text{-}Tyr^4\text{-}MeAla^5\text{-}Glu^6\text{-}Arg^7\text{-}MeIleu^8\text{-}Ala^9\text{-}OH$ (SEQ ID NO:16) | 0 |

Percent protection means % of reduction in ulceration area in the peptide-treated group in comparision to the control (vehicle) group
* and ** indicates statistically significant improvement versus control at the level of p < 0.001 and 0.005, respectively.

Percent protection means % of reduction in ulceration area in the peptide-treated group in comparison to the control (vehicle) group.

* and ** indicate statistically significant improvement versus control at the level of $p<0.001$ and 0.0005, respectively.

Example 8

Protective Effects of Peptides Against Inflammatory Response Induced by Chemical Insults The protective effect of peptides IV and 3b against the inflammatory response caused by sulfur mustard (SM) was assessed. Peptide IV and 3b (40 mg/kg) reduced the inflammatory response by 19% and 18%, respectively.

Figure 7:
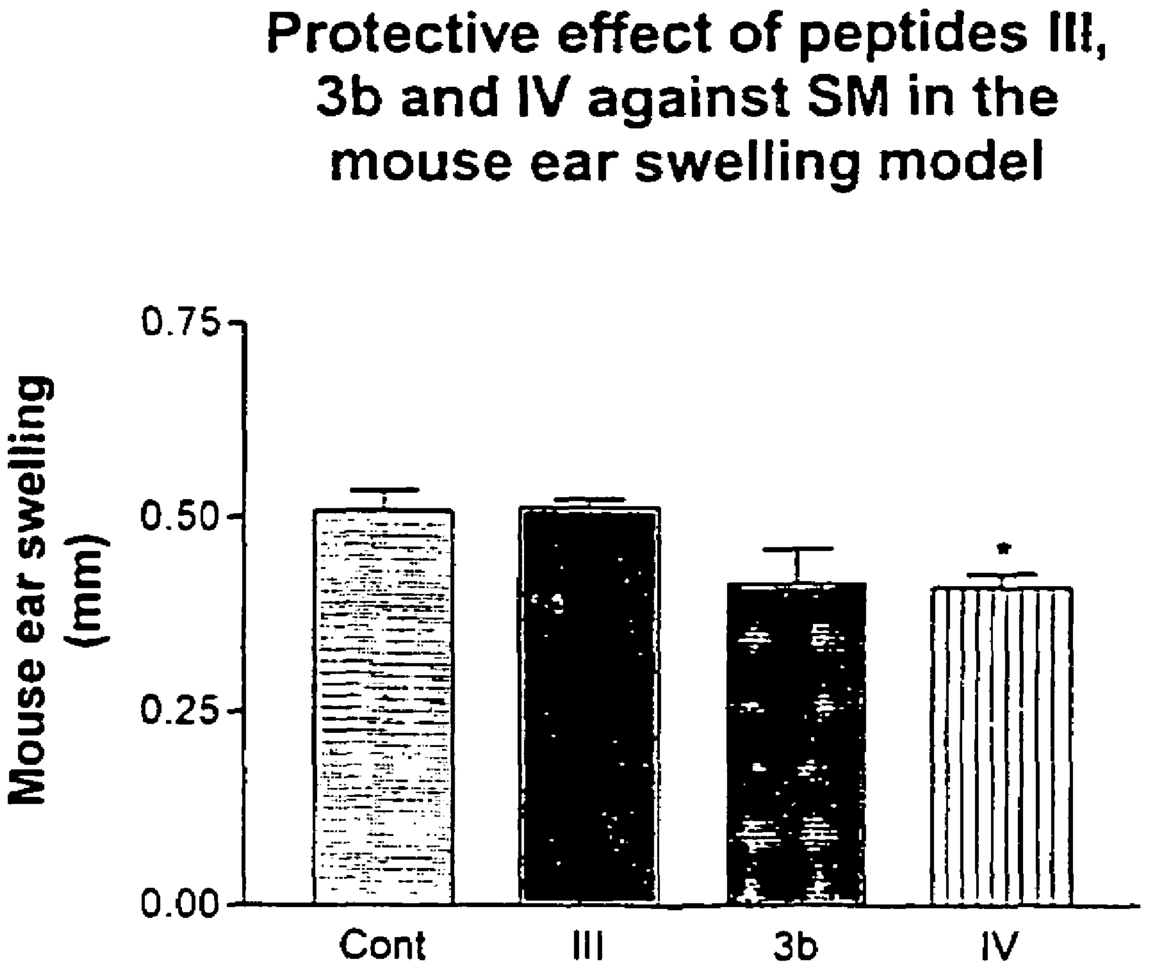
FIG. 7 demonstrates the protective effect of peptides III, 3b and IV against SM in the mouse inflammation (ear edema) model.

FIG. 7: Protective effect of peptides III, 3b and IV against SM in the mouse ear swelling model.

Male ICR mice (~25 g) were anesthetized by pentobarbital sodium 60 mg/kg ip (0.1 ml/25 g BW of 1.5% solution) and placed on their abdominal side. Anesthesia was maintained by 0.03 ml/25 g BW whenever needed. Peptides III, 3b and IV (dissolved in 0.9% NaCl) were injected intravenously (each peptide injected into different group of animals) at a single dose of 40 mg/kg body weight (volume of injection was 0.2 ml). Control (cont) animals received 0.9% NaCl injections. Within 5 min after injection, the outer side of each ear was exposed to 0.317 mg SM (5 μl of 1:20 dilution in dichloromethane). Mouse ear thickness was measured 48 hours after exposure using micrometer (Model PK-0505, Mitutoyo Corporation, Japan). Edema was assessed by the difference between ear thickness measured after and prior to exposure. Animals were sacrificed 48 hours after exposure. Results are the mean ±SE using the Mann Whitney U test for statistical evaluation of the difference between Cont and peptide IV group. The asterisk denotes statistical significance at the level of $*p<0.01$.

```
H-Lys1-Gly2-Asn3-Tyr4-MeAla5-Glu6-Arg7-Ileu8-Ala9-
OH (peptide 3b; SEQ ID NO:5)
```

```
H-Asp-Thr-Glu-Phe-Glu-Ala-Ala-Gly-Gly-Gly-Val-Arg-
OH (peptide IV; SEQ ID NO:2)
```

Example 9

Figure 8:
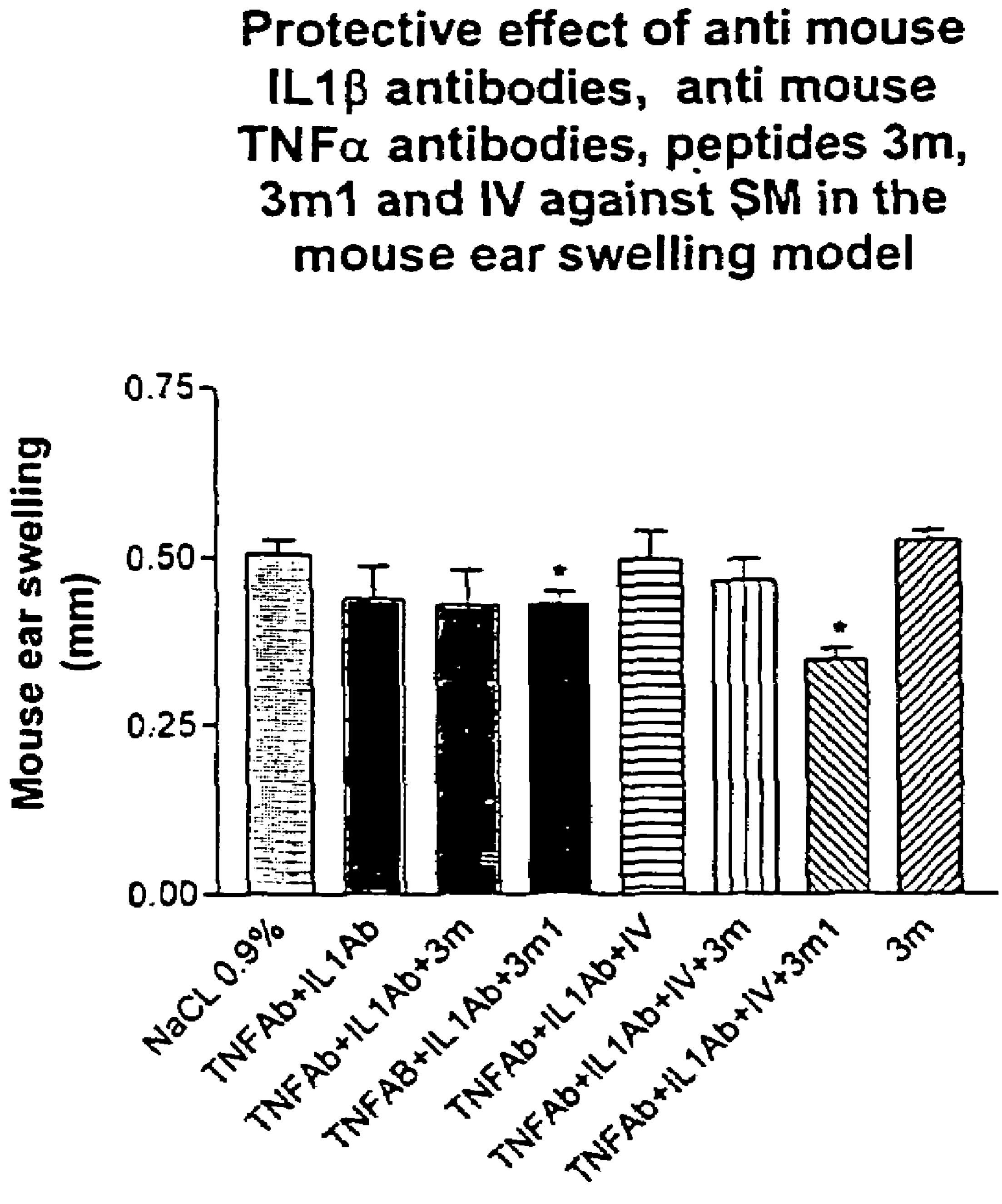
FIG. 8 shows the protective effect of anti mouse interleukin 1 beta (IL 1 beta) antibodies, anti mouse tumor necrosis factor alpha (TNF alpha) antibodies, peptides 3m, 3m1 and IV against SM in the mouse ear edema model.

Synergistic Anti-Inflammatory Effects of Novel Peptides with Anti-Inflammatory Agents The ability of the novel peptides of the invention to enhance the activity of known anti-inflammatory agents was tested using the novel peptides in conjunction with modulatory antibodies capable of neutralizing cytokines, which are inflammatory mediators FIG. 8 demonstrates the protective effect of the combinations of anti mouse IL1 beta antibodies, anti mouse TNF alpha antibodies, peptide IV and peptide 3 ml against sulfur mustard induced inflammatory response as expressed by mouse ear edema. This combination reduced SM-induced ear edema by 31%. Omission of peptide IV from this combination reduced mouse swelling by 15%. Peptide IV only has no protective effect. Thus, peptide IV had a synergistic effect on the protection of the combination of anti mouse IL1 beta antibodies, anti mouse TNF alpha antibodies, and peptide 3 ml.

Protocol Protective effect of anti mouse interleukin 1 beta (IL1 beta) antibodies, anti mouse tumor necrosis factor alpha (TNF alpha) antibodies, peptides 3 m, 3 ml and IV against SM in the mouse ear edema model.

Male ICR mice (~25 g) were anesthetized by pentobarbital sodium 60 mg/kg ip (0.1 ml/25 g BW of 1.5% solution) and placed on their abdominal side. Anesthesia was maintained by 0.03 ml/25 g BW whenever needed. Peptides 3 m, 3 ml, IV and IV (dissolved in 0.9% NaCl), and anti mouse IL1 beta (IL1Ab) antibodies and anti mouse TNF alpha antibodies (TNFAb) were tested for their ability to protect against SM-induced toxicity. The following combinations were prepared: a) 5 μg/injection anti mouse IL1 beta antibodies, 10 μg/injection anti mouse TNF alpha antibodies; b) 5 μg/injection anti mouse IL1 beta antibodies, 10 μg/injection anti mouse TNF alpha antibodies, 10 mg/kg 3 m; c) 5 μg/injection anti mouse IL1 beta antibodies, 10 μg/injection anti mouse TNF alpha antibodies, 10 mg/kg 3 ml; d) 5 μμg/injection anti mouse IL1 beta antibodies, 10 μg/injection anti mouse TNF alpha antibodies, 10 mg/kg IV; e) 5 μg/injection anti mouse IL1 beta antibodies, 10 μg/injection anti mouse TNF alpha antibodies, 10 mg/kg IV, 10 mg/kg 3 m; f) 5 μg/injection anti mouse IL1 beta antibodies, 10 μg/injection anti mouse TNF alpha antibodies, 10 mg/kg IV, 10 mg/kg 3m1; g) 10 mg/kg 3 m. All peptides and antibody dilutions were carried out with 0.9% NaCl. Volume of injection was 0.2 ml. Control animals received 0.9% NaCl injections. Within 5 min after injection, the outer side of each ear was exposed to 0.317 mg SM (5 μl of 1:20 dilution in dichloromethane). Mouse ear thickness was measured 48 hours after exposure using micrometer (Model PK-0505, Mitutoyo Corporation, Japan). Edema was assessed by the difference between ear thickness measured after and prior to exposure. Animals were sacrificed 48 hours after exposure. Results are the mean ±SE using the Mann Whitney U test for statistical evaluation of the difference between Cont and peptide IV group. Results are the mean ±SE using the Mann Whitney U test for statistical evaluation of the difference between 0.9% NaCl group and experimental groups. The asterisk denotes statistical significance at the level of $p<0.04$.

The same statistical significance was observed for the difference between the group of: 5 μg/injection anti mouse IL1 beta antibodies, 10 μg/injection anti mouse TNF alpha antibodies, 10 mg/kg 3 ml, and the group of: 5 μg/injection anti mouse IL1 beta antibodies, 10 μg/injection anti mouse TNF alpha antibodies, 10 mg/kg IV, 10 mg/kg 3 ml;

The same statistical significance was observed for the difference between the group of: 5 μg/injection anti mouse IL1 beta antibodies, 10 μg/injection anti mouse TNF alpha antibodies, 10 mg/kg IV, and the group of: 5 μg/injection anti mouse IL1 beta antibodies, 10 μg/injection anti mouse TNF alpha antibodies, 10 mg/kg IV, 10 mg/kg 3 ml

```
H-Lys-Gly-Asn-Tyr-Ser-Glu-Arg-Val-Gly-OH
(peptide 3m; SEQ ID NO:11)
```

```
H-Lys-Gly-His-Tyr-Ala-Glu-Arg-Val-Gly-OH
(peptide 3ml; SEQ ID NO:13)
```

```
H-Asp-Thr-Glu-Phe-Glu-Ala-Ala-Gly-Gly-Gly-Val-Arg-
OH (peptide IV; SEQ ID NO:2)
```

Example 10

Manufacture of a Medicament Containing Synthetic Peptides of the Invention

As used herein a "pharmaceutical composition" refers to a preparation of one or more of the peptides described herein, or physiologically acceptable salts or prodrugs thereof, with other chemical components such as physiologically suitable carriers and excipients. The purpose of a pharmaceutical composition is to facilitate administration of a compound to an organism.

The term "prodrug" refers to an agent, which is converted into an active parent drug in vivo. Prodrugs are often useful because in some instances they may be easier to administer than the parent drug. They may, for instance, be bioavailable by oral administration whereas the parent drug is not. The prodrug may also have improved solubility compared to the parent drug in pharmaceutical compositions.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Pharmaceutical compositions may also include one or more additional active ingredients, such as, but not limited to, conventional anti-migraine agents.

Pharmaceutical compositions of the present invention may be manufactured by processes well known in the art, e.g., by means of conventional mixing, dissolving, granulating, grinding, pulverizing, dragee-making, levigating, emulsifng, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate. In addition enterocoating are useful as it is desirable to prevent exposure of the peptides of the invention to the gastric environment.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the peptides for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated.

Determination of a therapeutically effective amount is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50%; inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, and all other relevant factors.

The following example is an illustration only of a method of treating a subject with a peptide according to the invention, in order to treat a pathological condition associated with tissue trauma or a related condition, and is not intended to be limiting.

The method includes the step of administering the protective peptide, in a pharmaceutically acceptable carrier as described above, to a subject to be treated. The medicament is administered according to an effective dosing methodology, preferably until a predefined endpoint is reached, such as a reduction or amelioration of the pathological condition in the subject.

The protective factors may be used for treatment and protection on the central and peripheral nervous systems against noxious stimuli caused by, but not limited to, chemicals, drugs, all kinds of irradiation and mechanical stress.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification. In addition, citation or identification of any reference in this application shall not be construed as an admission that such reference is available as prior art to the present invention.

What is claimed is:

1. A pharmaceutical composition comprising as an active ingredient a peptide selected from the group consisting of:

H-Lys-Gly-Asn-Tyr-Ala-Glu-Arg-Ileu-Ala-OH (SEQ ID NO: 1);

H-Asp-Thr-Glu-Phe-Glu-Ala-Ala-Gly-Gly-Gly-Val-Arg-OH (SEQ ID NO:2);

H-Thr-Thr-Asp-Thr-Glu-Phe-Glu-Ala-Ala-Gly-Gly-Gly-Val-Arg-OH (SEQ ID NO:4);

H-Lys-Gly-Asn-Tyr-MeAla-Glu-Arg-Ileu-Ala-OH (SEQ ID NO: 5);

H-Lys-Gly-Asn-Tyr-Ala-Glu-Arg-MeIleu-Ala-OH (SEQ ID NO:6);

H-Lys-MeGly-Asn-Tyr-Ala-Glu-Arg-Ileu-Ala-OH (SEQ ID NO:7);

H-Lys-MeGly-Asn-Tyr-Ala-Glu-Arg-MeIleu-Ala-OH (SEQ ID NO:8);

H-Lys-Gly-His-Tyr-Ala-Glu-Arg-Val-Gly-OH (SEQ ID NO: 13);

H-Lys-Gly-Asn-Tyr-Ala-Glu-Arg-Val-Gly-OH (SEQ ID NO: 10);

H-Lys-Ala-His-Tyr-Ser-Glu-Arg-Val-Gly-OH (SEQ ID NO: 12);

H-Lys-Ser-Arg-Thr-Thr-Ser-His-Gly-Arg-Val-Gly-OH (SEQ ID NO: 14)

H-Lys-Gly-Asn-Tyr-Ser-Glu-Arg-Val-Gly-OH (SEQ ID NO:11)

H-Lys-MeGly-Asn-Tyr-MeAla-Glu-Arg-MeIleu-Ala-OH (SEQ ID NO:16); and their N-methylated analogs, together with a pharmaceutically acceptable diluent or excipient.

2. The pharmaceutical composition of claim 1, further comprising at least one protease inhibitor present in an amount sufficient to prevent peptide degradation.

3. The pharmaceutical composition of claim 1, further comprising at least one additional anti-inflammatory agent.

4. The pharmaceutical composition of claim 3, wherein the additional anti-inflammatory agent is a chemokine modulator.

5. A method for protecting an individual against thermal or chemical induced burns which comprises administering to an individual in need of such treatment a therapeutically effective amount of the pharmaceutical composition of claim 1.

6. The method of claim 5, wherein the pharmaceutical composition is administered prior to onset of thermal or chemical induced burns.

7. The method of claim 5, wherein the pharmaceutical composition is administered after onset of thermal or chemical induced burns.

8. The method of claim 5, wherein the pharmaceutical composition is administered by parenteral injection.

9. The method of claim 8, wherein the injection is selected from the group consisting of intravenous, intramuscular, intradermal, intralesional, intrathecal and subcutaneous injections.

10. The method of claim 5, wherein the pharmaceutical composition is administered via transdermal, oral, rectal, topical, nasal, inhalation or ocular modes of treatment.

11. A peptide is selected from the group consisting of:

H-Lys-Gly-Asn-Tyr-Ala-Glu-Arg-Ileu-Ala-OH (SEQ ID NO: 1);

H-Asp-Thr-Glu-Phe-Glu-Ala-Ala-Gly-Gly-Gly-Val-Arg-OH (SEQ ID NO:2);

H-Thr-Thr-Asp-Thr-Glu-Phe-Glu-Ala-Ala-Gly-Gly-Gly-Val-Arg-OH (SEQ ID NO:4);

H-Lys-Gly-Asn-Tyr-MeAla-Glu-Arg-Ileu-Ala-OH (SEQ ID NO: 5);

H-Lys-Gly-Asn-Tyr-Ala-Glu-Arg-MeIleu-Ala-OH (SEQ ID NO:6);

H-Lys-MeGly-Asn-Tyr-Ala-Glu-Arg-Ileu-Ala-OH (SEQ ID NO:7);

H-Lys-MeGly-Asn-Tyr-Ala-Glu-Arg-MeIleu-Ala-OH (SEQ ID NO: 8);

H-Lys-Gly-His-Tyr-Ala-Glu-Arg-Val-Gly-OH (SEQ ID NO: 13)

H-Lys-Gly-Asn-Tyr-Ala-Glu-Arg-Val-Gly-OH (SEQ ID NO: 10)

H-Lys-Ala-His-Tyr-Ser-Glu-Arg-Val-Gly-OH (SEQ ID NO: 12)

H-Lys-Ser-Arg-Thr-Thr-Ser-His-Gly-Arg-Val-Gly-OH (SEQ ID NO: 14)

H-Lys-Gly-Asn-Tyr-Ser-Glu-Arg-Val-Gly-OH (SEQ ID NO:11)

H-Lys-MeGly-Asn-Tyr-MeAla-Glu-Arg-MeIleu-Ala-OH (SEQ ID NO:16); and a methylated analog thereof.

12. The peptide according to claim 11 consisting of the amino acid sequence H-Lys-Gly-Asn-Tyr-Ser-Glu-Arg-Val-Gly-OH (SEQ ID NO:11).

13. The peptide according to claim 11 consisting of the amino acid sequence H-Lys-Gly-His-Tyr-Ala-Glu-Arg-Val-Gly-OH (SEQ ID NO: 13).

* * * * *

UNITED STATES PATENT AND TRADEMARK OFFICE

CERTIFICATE OF CORRECTION

PATENT NO. : 7,238,656 B2
APPLICATION NO. : 10/790888
DATED : July 3, 2007
INVENTOR(S) : Wormser It is certified that error appears in the above-identified patent and that said Letters Patent is hereby corrected as shown below:

Column 26:

Line 66 (claim 1, line 24), after "(SEQ ID NO: 14)", insert -- ; --.

Column 27:

Line 2 (claim 1, line 26), after "(SEQ ID NO: 11)", insert -- ; --.
Line 35 (claim 11, line 1), after "A peptide", delete "is".

Column 28:

Line 16 (claim 11, line 17), after "(NO: 13)", insert -- ; --.
Line 18 (claim 11, line 19), after "(NO: 10)", insert -- ; --.
Line 20 (claim 11, line 21), after "(NO: 12)", insert -- ; --.
Line 22 (claim 11, line 23), after "(SEQ ID NO: 14)", insert -- ; --.
Line 24 (claim 11, line 25), after "(NO: 11)", insert -- ; --.

Signed and Sealed this

Twenty-first Day of August, 2007

JON W. DUDAS
*Director of the United States Patent and Trademark Office*